United States Patent
Shinozaki et al.

(10) Patent No.: US 11,285,042 B2
(45) Date of Patent: Mar. 29, 2022

(54) COOLING TOOL AND TREATMENT TOOL USED IN CRYOTHERAPY

(71) Applicant: SHARP KABUSHIKI KAISHA, Sakai (JP)

(72) Inventors: Daisuke Shinozaki, Sakai (JP); Yuka Utsumi, Sakai (JP); Satoru Motonami, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 450 days.

(21) Appl. No.: 16/462,685

(22) PCT Filed: Nov. 17, 2017

(86) PCT No.: PCT/JP2017/041389
§ 371 (c)(1),
(2) Date: May 21, 2019

(87) PCT Pub. No.: WO2018/097045
PCT Pub. Date: May 31, 2018

(65) Prior Publication Data
US 2020/0078213 A1    Mar. 12, 2020

(30) Foreign Application Priority Data
Nov. 22, 2016 (JP) .............................. JP2016-227104

(51) Int. Cl.
A61F 7/10 (2006.01)
A61F 7/02 (2006.01)

(52) U.S. Cl.
CPC ........ *A61F 7/10* (2013.01); *A61F 2007/0247* (2013.01); *A61F 2007/0292* (2013.01); *A61F 2007/108* (2013.01)

(58) Field of Classification Search
CPC ...... A61F 2007/0247; A61F 2007/0249; A61F 2007/0253; A61F 2007/0292; A61F 2007/108; A61F 7/10
See application file for complete search history.

(56) References Cited

U.S. PATENT DOCUMENTS

2012/0296402 A1* 11/2012 Kotter .................. A61F 7/10
607/108

FOREIGN PATENT DOCUMENTS

| JP | H07-095998 A | 4/1995 |
| WO | 2016/002596 A1 | 1/2016 |
| WO | 2017/187774 A1 | 11/2017 |

* cited by examiner

*Primary Examiner* — Tigist S Demie
(74) *Attorney, Agent, or Firm* — ScienBiziP, P.C.

(57) ABSTRACT

A human body is cooled at an appropriate temperature, and a sufficient usage time is ensured. A cooling tool according to one aspect of the present invention is a cooling tool for cooling a human body, including a freezing material 30a that undergoes a phase change at a particular temperature and a first container containing the freezing material 30a. The first container transfers heat between the human body and the freezing material at a contact surface in contact with the skin of the human body. At least the contact surface has a thermal effusivity within the possible range of thermal effusivity of the skin of the human body. The contact surface may have a thermal effusivity (J/(m2~S1/2·K)) of 1,000 to 2,000.

6 Claims, 11 Drawing Sheets

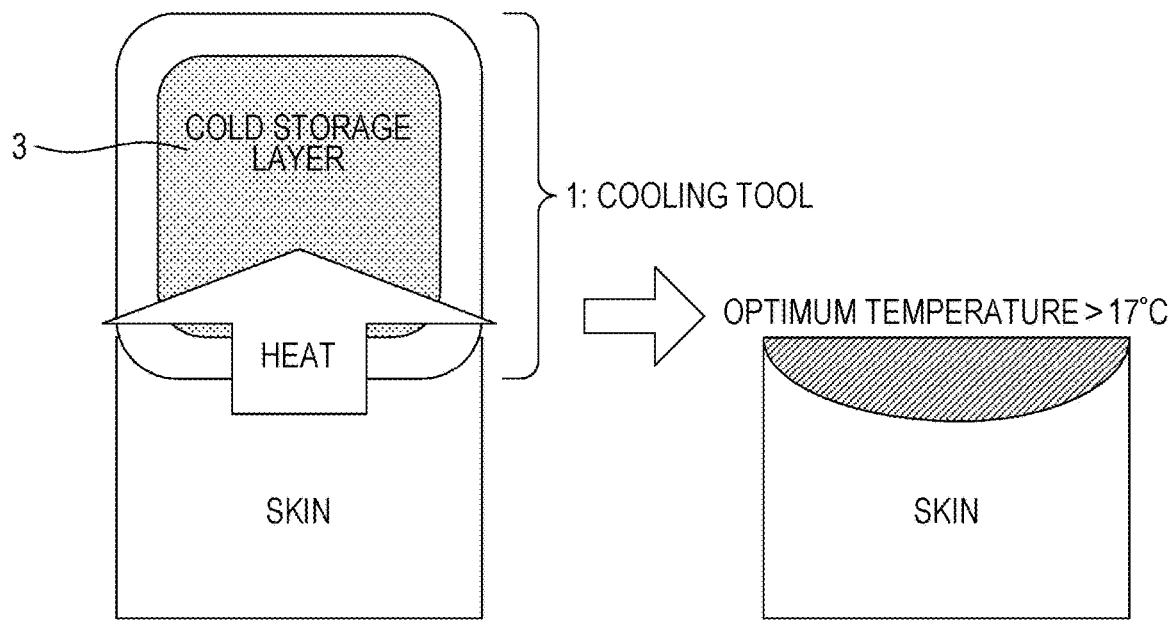

| PURPOSE | AREA OF APPLICATION | SKIN TEMPERATURE | TIME |
|---|---|---|---|
| FIRST AID FOR HEATSTROKE OR OTHER CONDITION | ARMPIT, NECK, OR GROIN (AREA WHERE THIGH JOINS BODY) | CONTINUE ACTIVE COOLING TREATMENT UNTIL DEEP BODY TEMPERATURE IS ON ORDER OF 38°C | 1 HOUR |
| ·DECREASE BLOOD FLOW VOLUME AND BLEEDING VOLUME. DECREASE CELLULAR METABOLISM AND MINIMIZE SECONDARY DAMAGE DUE TO ISCHEMIA ·DECREASE PRODUCTION OF PAIN-PRODUCING SUBSTANCES BY COOLING ·DECREASE SENSORY IMPULSES TO CENTRAL NERVOUS SYSTEM BY SLOWDOWN OF SENSORY RECEPTOR RESPONSE AND RETARDATION OF STIMULUS TRANSMISSION THROUGH SENSORY NERVES → PAIN-RELIEVING EFFECT | SURGERY AREA | 20°C TO 25°C (REHABILITATION AFTER SURGERY) | 0.5 HOURS |
| IMPROVE CONCENTRATION RELAXATION | FOREHEAD, NECK, OR OTHER AREA | 33°C (TEMPERATURE COMFORTABLE FOR HUMANS) | 1 TO 2 HOURS |
| PREVENT HEATSTROKE | FOREHEAD, NECK, OR OTHER AREA | 12°C TO 20°C (THERMOREGULATION IN PEOPLE WITH SPINAL CORD INJURIES) | 2 TO 3 HOURS |
| MAINTAIN OPTIMUM TEMPERATURE | MUSCLE FREQUENTLY USED FOR EACH EXERCISE | AROUND 27°C (OPTIMUM TEMPERATURE FOR MUSCLES) | |

FIG. 5

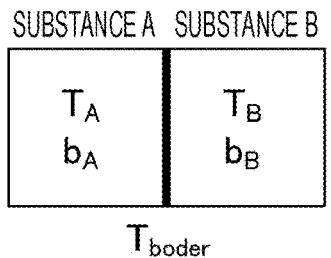

$T_{boder}$ : BORDER SURFACE TEMPERATURE
$T_A$ : TEMPERATURE OF SUBSTANCE A
$b_A$ : THERMAL EFFUSIVITY OF SUBSTANCE A
$T_B$ : TEMPERATURE OF SUBSTANCE B
$b_B$ : THERMAL EFFUSIVITY OF SUBSTANCE B

FIG. 6

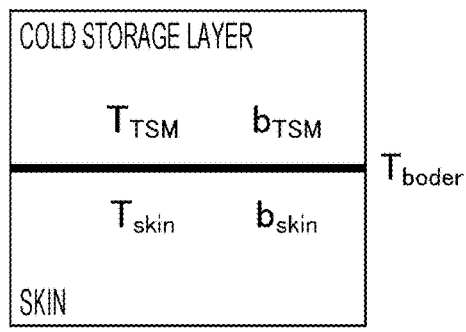

$T_{boder}$ : BORDER SURFACE TEMPERATURE
$T_{TSM}$ : TEMPERATURE OF COLD STORAGE LAYER
$b_{TSM}$ : THERMAL EFFUSIVITY OF COLD STORAGE LAYER
$T_{skin}$ : TEMPERATURE OF SKIN
$b_{skin}$ : THERMAL EFFUSIVITY OF SKIN

FIG. 7

METHOD FOR CALCULATING THERMAL CONDUCTIVITY OF MULTILAYER OBJECT

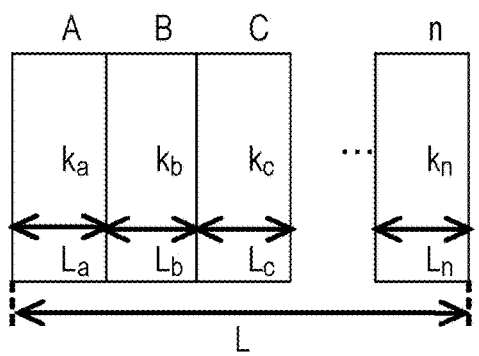

$$k_{total} = \frac{L}{\frac{L_a}{k_a} + \frac{L_b}{k_b} + \frac{L_c}{k_c} + \cdots + \frac{L_n}{k_n}}$$

*CONTACT RESISTANCE IS NOT CONSIDERED

FIG. 8

| | | SAMPLE ① |
|---|---|---|
| SECTIONAL VIEW | | 10 mm [TBAB layered structure] |
| MATERIAL | PACKAGE | NYLON (NY)_10 μm |
| | | LINEAR LOW-DENSITY POLYETHYLENE (LL)_50 μm |
| | | – |
| | | – |
| THERMAL CONDUCTIVITY: $\lambda$ (W/m·K) | | 0.419 |
| THERMAL DIFFUSIVITY: $\alpha$ (m$^2$/s) | | $1.743 \times 10^{-7}$ |
| THERMAL EFFUSIVITY: b (J/s$^{1/2}$·m$^2$·K) | | 1,003 |

SAMPLE ① — $L_n/k_n$

| | | | | |
|---|---|---|---|---|
| NY | L | 10 | 29.41176 | |
| | k | 0.34 | | |
| LL | L | 50 | 151.5152 | |
| | k | 0.33 | | |
| TBAB | L | 10000 | 23809.52 | |
| | k | 0.42 | | |
| LL | L | 50 | 151.5152 | |
| | k | 0.33 | | |
| NY | L | 10 | 29.41176 | |
| | k | 0.34 | | |
| SKIN | | | | |

$L_{total} = 10120$
$\lambda k_{total} = 0.419$
$\alpha = 1.743E-07$
$b = 1003$

FIG. 9

| | | SAMPLE ① | SAMPLE ② | SAMPLE ③ |
|---|---|---|---|---|
| SECTIONAL VIEW | | TBAB | TBAB | TBAB |
| MATERIAL | PACKAGE | NYLON (NY)_10 μm | ALUMINUM-METALLIZED POLYETHYLENE TEREPHTHALATE (vmPET)_10 μm | NYLON (NY)_10 μm |
| | | LINEAR LOW-DENSITY POLYETHYLENE (LL)_50 μm | LOW-DENSITY POLYETHYLENE (LL)_50 μm | POLYETHYLENE (PE)_20 μm |
| | | – | – | ALUMINUM (AL)_5 μm |
| | | – | – | LOW-DENSITY POLYETHYLENE (LL)_50 μm |
| THERMAL CONDUCTIVITY: $\lambda$ (W/m·K) | | 0.419 | 0.417 | 0.420 |
| THERMAL DIFFUSIVITY: $\alpha$ (m$^2$/s) | | $1.743 \times 10^{-7}$ | $1.738 \times 10^{-7}$ | $1.747 \times 10^{-7}$ |
| THERMAL EFFUSIVITY: b (J/s$^{1/2}$·m$^2$·K) | | 1,003 | 1,001 | 1,004 |

*THERMAL CONDUCTIVITY IS CALCULATED AS "THERMAL CONDUCTIVITY OF MULTILAYER OBJECT"

FIG. 10A
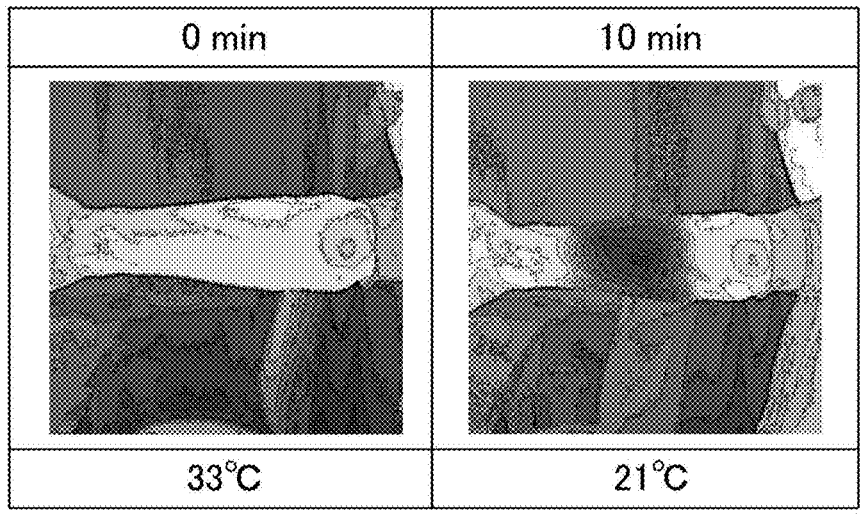
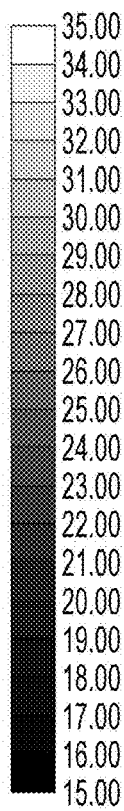
FIG. 10B
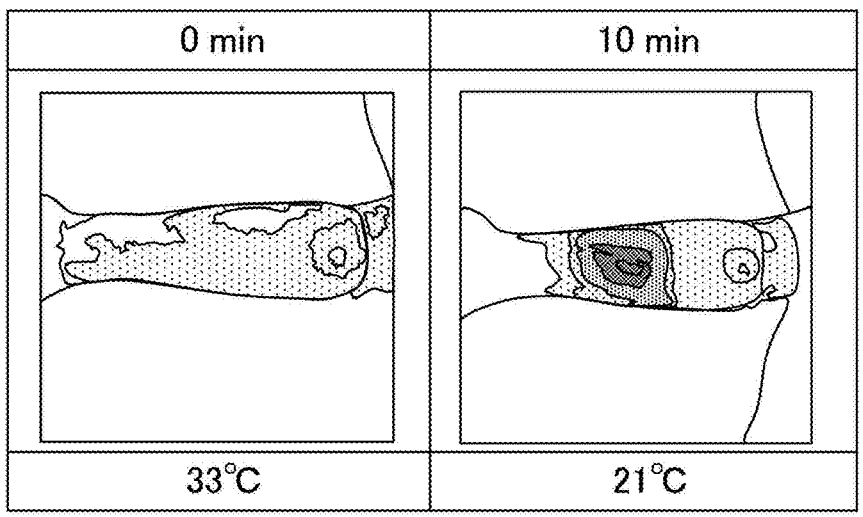
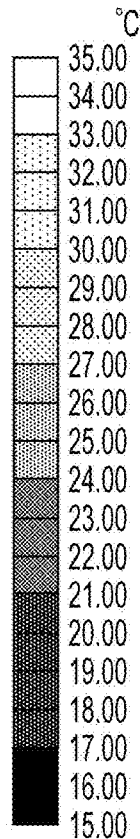

FIG. 14

| | | SAMPLE ① | SAMPLE ② | SAMPLE ③ |
|---|---|---|---|---|
| SECTIONAL VIEW | | NaCl | NaCl | NaCl |
| MATERIAL | PACKAGE | NYLON (NY)_10 μm | ALUMINUM-METALLIZED POLYETHYLENE TEREPHTHALATE (vmPET)_10 μm | NYLON (NY)_10 μm |
| | | LINEAR LOW-DENSITY POLYETHYLENE (LL)_50 μm | LOW-DENSITY POLYETHYLENE (LL)_50 μm | POLYETHYLENE (PE)_20 μm |
| | | – | – | ALUMINUM (AL)_5 μm |
| | | – | – | LOW-DENSITY POLYETHYLENE (LL)_50 μm |
| THERMAL CONDUCTIVITY: $\lambda$ (W/m·K) | | 0.589 | 0.584 | 0.590 |
| THERMAL DIFFUSIVITY: $\alpha$ (m²/s) | | $1.537 \times 10^{-7}$ | $1.524 \times 10^{-7}$ | $1.503 \times 10^{-7}$ |
| THERMAL EFFUSIVITY: $b$ (J/s$^{1/2}$·m²·K) | | 1,502 | 1,495 | 1,503 |

*THERMAL CONDUCTIVITY IS CALCULATED AS "THERMAL CONDUCTIVITY OF MULTILAYER OBJECT"

FIG. 15A

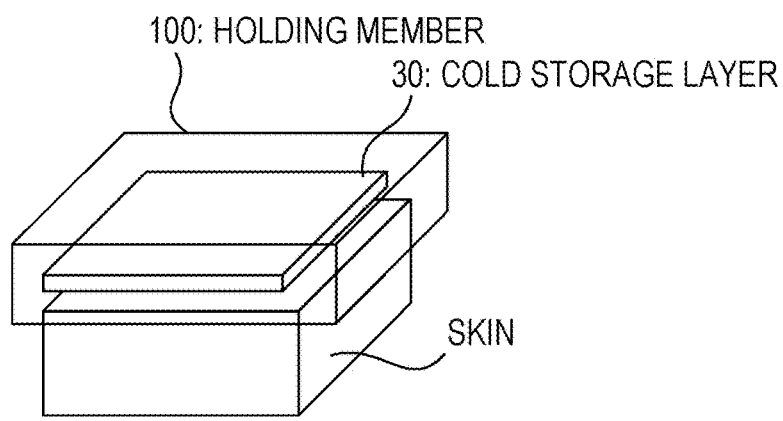

100: HOLDING MEMBER
30: COLD STORAGE LAYER
SKIN

FIG. 15B
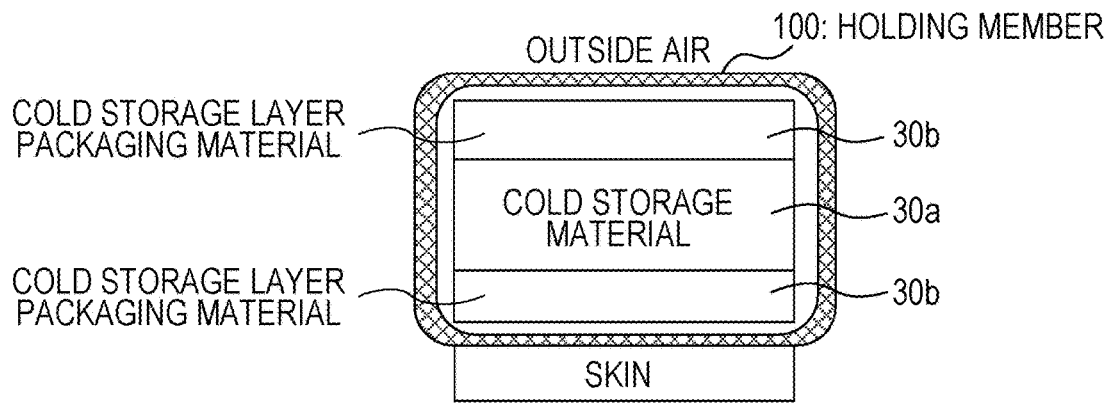
FIG. 15C
EXAMPLE OF HOLDING MEMBER
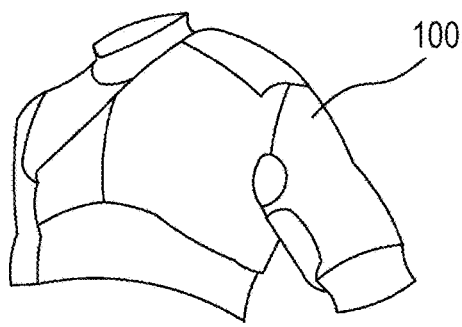
FIG. 16
| HUMAN BODY | $T_{boder}$ | COOLING MATERIAL |
|---|---|---|
| $T_{skin}$ $b_{skin}$ | | $T_{TSM}$ $b_{TSM}$ |
$T_{boder}$ : BORDER TEMPERATURE
$T_{skin}$ : SKIN BORDER TEMPERATURE
$T_{TSM}$ : COLD STORAGE MATERIAL BORDER TEMPERATURE
$b_{skin}$ : SKIN THERMAL EFFUSIVITY
$b_{TSM}$ : COLD STORAGE MATERIAL THERMAL EFFUSIVITY

COOLING TOOL AND TREATMENT TOOL USED IN CRYOTHERAPY

TECHNICAL FIELD

The present invention relates to cooling tools for cooling a human body and treatment tools used in cryotherapy.

BACKGROUND ART

There is a cooling therapy conventionally known as icing, cryotherapy, or the like. This cryotherapy involves cooling a hot area or the entire body of a human, for example, by a technique such as applying cold air to the human body or bringing a cooling material into contact with the skin of the human body. PTL 1 discloses a cooling material that gives a comfortable feel and fit on the head of a human body and that offers sufficient cooling performance. This cooling material includes a plurality of pieces of freezing material with a thickness of 15 to 35 mm that are coupled to each other in the horizontal direction and a non-freezing material with a thickness of 5 to 15 mm. The freezing material and the non-freezing material are stacked on top of each other and are contained in an outer bag.

CITATION LIST

Patent Literature

PTL 1: Japanese Unexamined Patent Application Publication No. 7-95998

SUMMARY OF INVENTION

Technical Problem

When a cooling material is used to cool an affected area in cryotherapy, the cooling material may be too cold for the human body and may therefore be difficult to use for a long period of time, which may result in an insufficient cooling time. Accordingly, attempts have been made to maintain an appropriate skin temperature by placing a fabric or other material between the cooling material and the skin. Although the cooling material disclosed in PTL 1 is intended for the human body, there is no consideration of thermophysical properties or the temperature range during use; therefore, the cooling material removes too much heat from the human body when brought into direct contact with the skin of the human body.

Humans have a nerve called TRPA1, which functions to cause them to perceive "pain" when the skin temperature decreases to 17° C. or lower. Thus, when a human body is cooled, sufficient care needs to be taken to the skin temperature so that this nerve does not function. A cooling material that decreases the skin temperature to 17° C. or lower is difficult to use for a long period of time and could even cause frostbite, depending on the situation. Although PTL 1 discloses a cooling material intended for use on the human body, there is no mention of, for example, the thermophysical properties of the material used as the cooling material or the temperature range of the freezing material; therefore, TRPA1 described above could function. Such cooling materials are not suitable for wearing for a long period of time.

In addition, the purpose and means differ greatly between first aid for inflammation due to acute traumatic injuries and rehabilitation or relief care; however, no cooling tool has been proposed that differentiates between these situations.

In view of the foregoing, an object of the present invention is to provide a cooling tool and a treatment tool used in cryotherapy that can cool a human body at an appropriate temperature while ensuring a sufficient usage time.

Solution to Problem

To achieve the foregoing object, the present invention employs the following solution. Specifically, a cooling tool according to one aspect of the present invention is a cooling tool for cooling a human body, including a freezing material that undergoes a phase change at a particular temperature and a first container containing the freezing material. The first container transfers heat between the human body and the freezing material at a contact surface in contact with the skin of the human body. At least the contact surface has a thermal effusivity within the possible range of thermal effusivity of the skin of the human body.

Advantageous Effects of Invention

The cooling tool according to the aspect of the present invention can cool a human body at an appropriate temperature and can cool the skin of the human body at a mild temperature for a long period of time without causing discomfort such as feeling too cold when brought into direct contact with the skin of the human body.

BRIEF DESCRIPTION OF DRAWINGS

FIG. 1 is an illustration showing the concept of a cooling tool according to a first embodiment.

FIG. 2 is a table showing the purpose of treatment, the affected area, the skin temperature, and the usage time of a cooling material in cryotherapy.

FIG. 5 is a schematic view showing the relationship between temperature and thermal effusivity.

FIG. 6 is a schematic view showing the border between a cold storage layer and the skin of a human body.

FIG. 7 is an illustration showing a method for calculating the thermal conductivity of a multilayer object.

FIG. 8 is a table showing the thermophysical properties of a cold storage layer.

FIG. 9 is a table showing the thermophysical properties of cold storage layers.

FIG. 10A is an illustration (contour plot) showing the results of a skin surface temperature measurement with the cooling tool according to the first embodiment.

FIG. 10B is an illustration (line diagram) showing the results of the skin surface temperature measurement with the cooling tool according to the first embodiment.

FIG. 14 is a table showing the thermophysical properties of buffer layers.

FIG. 15A is a schematic view showing the configuration of a cooling tool and a treatment tool according to Example 3.

FIG. 15B is a schematic view showing the configuration of the cooling tool and the treatment tool according to Example 3.

FIG. 15C is an illustration showing an example application.

FIG. 16 is a schematic view showing the border between a cold storage layer and the skin of a human body.

DESCRIPTION OF EMBODIMENTS

Figure 3:
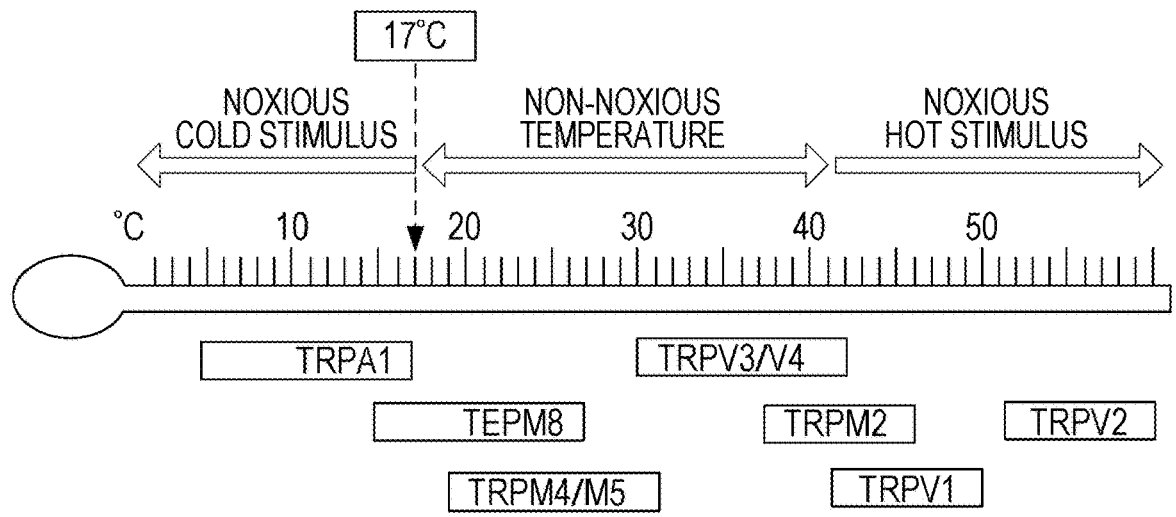
FIG. 3 is an illustration showing the activation temperature thresholds of temperature-sensitive TRPA channels in the human body.

The inventors have focused on the fact that, when a conventional cooling material is used to cool an affected area, the cooling material is too cold for the human body and is therefore difficult to use for a long period of time, which results in an insufficient cooling time. The inventors have found that an appropriate skin temperature and a sufficient usage time can be achieved through the use of a thermal storage material that undergoes a phase change at a particular temperature within a temperature range appropriate for cooling the human body and that has a thermal effusivity within the possible range of thermal effusivity of the skin of the human body, which has led to the present invention.

Specifically, a cooling tool according to one aspect of the present invention is a cooling tool for cooling a human body, including a freezing material that undergoes a phase change at a particular temperature and a first container containing the freezing material. The first container transfers heat between the human body and the freezing material at a contact surface in contact with the skin of the human body. At least the contact surface has a thermal effusivity within the possible range of thermal effusivity of the skin of the human body.

Thus, the inventors have made it possible to cool a human body at an appropriate temperature while ensuring a sufficient usage time. Embodiments of the present invention will hereinafter be specifically described with reference to the drawings.

First Embodiment

FIG. 1 is an illustration showing the concept of a cooling tool according to this embodiment. A cooling tool 1 includes a cold storage layer 3. The thermal identification of the cold storage layer 3 is specified as follows: it includes a thermal storage material that has a thermal effusivity within the possible range of thermal effusivity of the skin of the human body. The cooling tool 1 according to this embodiment can cool the skin of a human body at a mild temperature for a long period of time without causing discomfort such as feeling too cold when brought into direct contact with the skin of the human body.

FIG. 2 is a table showing the purpose of treatment, the affected area, the skin temperature, and the usage time of a cooling material in cryotherapy. To administer first aid for heatstroke or other condition, a cooling material is applied to the armpits, neck, or groin of the human body. As for the skin temperature in this case, active cooling treatment is continued until the deep body temperature is on the order of 38° C. In this case, the cooling material is used for 1 hour.

Cooling for decreasing blood flow volume and bleeding volume is expected to decrease cellular metabolism and minimize secondary damage due to ischemia. Other purposes of cooling include decreasing the production of pain-producing substances by cooling and decreasing spacing impulses to the central nervous system by the slowdown of sensory receptor response and the retardation of stimulus transmission through sensory nerves. For such cooling, the cooling material is applied to a surgery area, and the skin temperature is 20° C. to 25° C. The cooling material is used for 0.5 hours.

In the case of cooling for improving concentration and relaxation, the cooling material is applied to the forehead, neck, or other area, and the skin temperature is a temperature comfortable for humans, for example, 33° C. The cooling material is used for 1 to 2 hours. In the case of cooling for preventing heatstroke, the cooling material is applied to the forehead, neck, or other area, and the skin temperature is, for example, 12° C. to 20° C. for thermoregulation in people with spinal cord injuries. The cooling material is used for 2 to 3 hours. In the case of cooling for maintaining the optimum temperature, the cooling material is applied to a muscle frequently used for each exercise, and the skin temperature is around 27° C., which is the optimum temperature for muscles. The cooling material is used for 2 to 3 hours.

FIG. 3 is an illustration showing the activation temperature thresholds of temperature-sensitive TRPA channels in the human body. "Pain" occurs in the human body when a stimulus applied to a nociceptor present at a nerve ending is transmitted to the brain. Such nerve ending receptors include receptors corresponding to various stimuli, which are called "TRP receptors". These receptors send signals in different temperature ranges. For cold stimuli, as shown in FIG. 3, the TRPA1 channel is activated at "17° C. or lower". That is, when a human receives a stimulus that decreases the skin temperature to 17° C. or lower, he or she perceives it as pain; therefore, care needs to be taken to ensure that the skin temperature does not fall below 17° C. if cooling is necessary for a long period of time.

Example 1

Figure 4A:
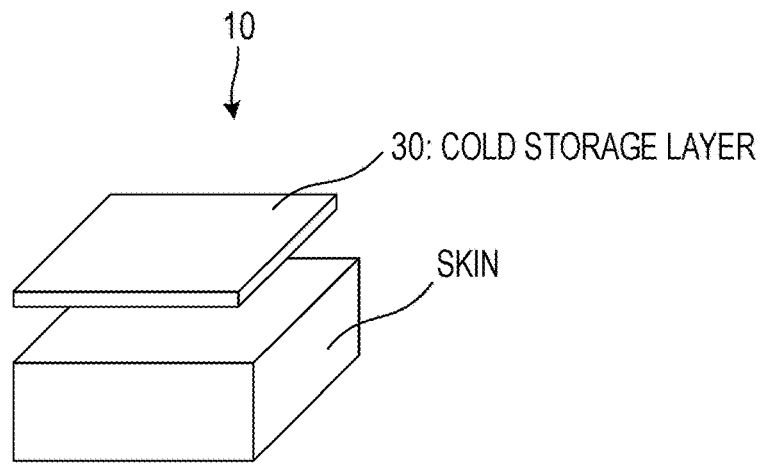
FIG. 4A is a schematic view showing a cooling tool according to Example 1.
Figure 4B:
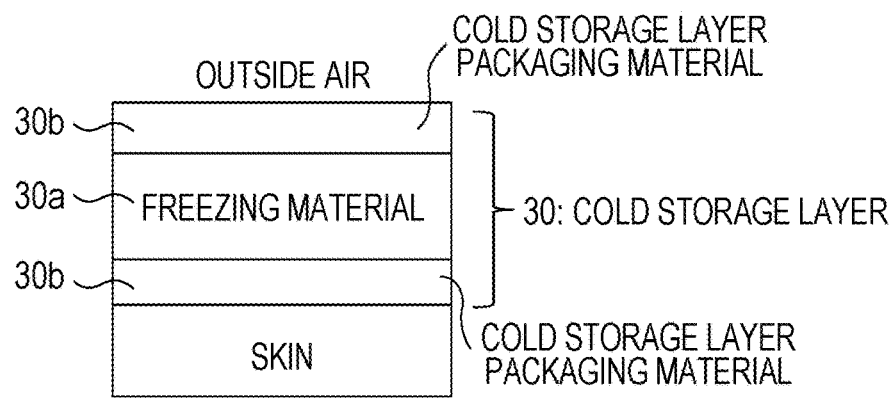
FIG. 4B is a schematic view showing the cooling tool according to Example 1.

FIGS. 4A and 4B are schematic views showing a cooling tool according to Example 1. This cooling tool 10 is composed of a cold storage layer 30. The cold storage layer 30 includes a freezing material 30a containing a thermal storage material that freezes at a particular temperature and that has a thermal effusivity close to that of the skin of the human body and a cold storage layer packaging material 30b having the freezing material 30a packed therein. The cold storage layer packaging material 30b forms a first container. The freezing material 30a is a thermal storage material that undergoes a phase change at a particular temperature and that has a thermal effusivity close to that of the skin of the human body. The cold storage layer 30, which is composed of the freezing material 30a and the cold storage layer packaging material 30b, also has a thermal effusivity close to that of the skin of the human body. The freezing material 30a used and described in this example is a thermal storage material containing TBAB in a concentration of 40% by weight; however, the cold storage layer need not necessarily include this thermal storage material, but may include any thermal storage material having a thermal effusivity close to that of the skin of the human body. Furthermore, it is more preferred that the thermal storage material or thermal storage layer have a thermal effusivity within the possible range of thermal effusivity of the skin of the human body.

(Relationship Between Temperature and Thermal Effusivity)

Thermal effusivity refers to the ability of an object to remove heat from another object through a contact surface in contact with the other object (hereinafter also referred to as "border surface"). Thermal effusivity (b) is represented by equation (1):

[Math. 1]

$$b = \sqrt{\rho c \lambda} \, (J/(m^2 \cdot S^{1/2} \cdot K)) \tag{1}$$

λ: thermal conductivity (W/m·K), ρ: density (kg/m³), c: specific heat (J/kg·K)

FIG. 5 is a schematic view showing the relationship between temperature and thermal effusivity. When two objects at different temperatures (substances A and B) are in contact with each other, the temperature $T_{boder}$ of the border surface is represented by equation (2):

[Math. 2]

$$T_{boder} = T_A + (T_B - T_A)\frac{T_B}{b_B + b_A} \tag{2}$$

$T_A$: temperature of substance A, $T_B$: temperature of substance B, $b_A$: thermal effusivity of substance A, $b_B$: thermal effusivity of substance B If the two objects (substances A and B) have equal thermal effusivity ($b_A = b_B$), the temperature of the border surface is represented by equation (3):

[Math. 3]

$$T_{boder} = \frac{T_A + T_B}{2} \tag{3}$$

That is, as shown in equation (3), the temperature $T_{boder}$ of the border surface is expressed only by the temperatures of the two objects (substances A and B). This indicates that the temperature distribution is identical to that without the border surface.

FIG. 6 is a schematic view showing the border between the cold storage layer and the skin of the human body. If the relationship between the thermal effusivities of the two objects described above is applied to this example, the temperature $T_{boder}$ of the border surface is determined by the temperature $T_{TSM}$ of the cold storage layer and the temperature $T_{skin}$ of the skin when the thermal effusivity $b_{TSM}$ of the cold storage layer (TSM: Thermal Storage Material (cold storage layer)) and the thermal effusivity $b_{skin}$ of the skin are substantially equal. Hence, the temperature $T_{boder}$ of the border surface can be represented by equation (4).

[Math. 4]

$$T_{boder} = \frac{T_{skin} + T_{TSM}}{2} \tag{4}$$

Thus, equation (4) is satisfied if the thermal effusivity of the cold storage layer is specified as substantially equal to the thermal effusivity of the skin of the human body. This indicates that the temperature spreads uniformly as if they were a single substance without any border. In this state, it is possible to alleviate a thermal imbalance such as the removal of too much heat by the cold storage layer.

(Freezing Material)

Next, a freezing material (thermal storage material) satisfying the thermal effusivity described above will be discussed. Although the thermal effusivity ($T_{skin}$) of the human body varies depending on the specific area of the human body, it is said to be approximately expressed as $1{,}000 < T_{skin} < 1{,}740$ (J/(m²·s^{1/2}·k)) (paper (1): Atsumasa Yoshida "Thermal Properties of Skin", Mechanical Engineering Antecedent, Graduate School of Engineering, Osaka Prefecture University, URL: <http://www.netsubussei.jp/group/SKyoshida.pdf>; paper (2): Tatsuo Togawa, Ph.D. "A Study on Imaging of Thermal Properties of the Skin", Institute of Biomaterials and Bioengineering, Tokyo Medical and Dental University, URL: <https://kaken.nii.ac.jp/ja/grant/KAKENHI-PROJECT-09480251/>).

Table 1 summarizes latent heat thermal storage materials (PCM: Phase Change Materials) having thermal effusivities close to that of the human body.

TABLE 1

| | Thermal effusivity (J/(m² · S^{1/2} · K)) | Melting point (° C.) |
|---|---|---|
| TBAB | 1,004.4 | 11.8 |
| Water | 1,574.2 | 0 |
| Paraffin | 485.4 | 6, 10, 18 |

Here, if a temperature that does not apply a cold stimulus to the skin of the human body when the cooling tool is brought into contact with the skin (a temperature that does not stimulate TRPA1) is considered, it is preferred that the temperature $T_{boder}$ of the border surface be higher than 17° C. That is, it is preferred to satisfy inequality (5):

[Math. 5]

$$T_{boder} = \frac{T_{skin} + T_{TSM}}{2} > 17° \text{ C.} \tag{5}$$

If the surface temperature of the skin of the human body is assumed to be about 31° C., a cold storage layer temperature $T_{TSM}$ of 5° C. or higher is probably sufficient from inequality (5). On the other hand, if there is too large a temperature difference between the surface temperature of the skin and the surface temperature of the cold storage layer, a stimulus due to the temperature difference causes discomfort even if inequality (5) is satisfied. Thus, it is probably preferred to select a thermal storage material so that there is no temperature difference between the surface temperature of the skin and the surface temperature of the freezing material.

As shown in Table 1, the thermal effusivities (J/(m²·S^{1/2}·K)) of the individual thermal storage materials are as follows: TBAB has a thermal effusivity of 1,004.4, water has a thermal effusivity of 1,574.2, and paraffin has a thermal effusivity of 485.4. TBAB and water have thermal effusivities close to that of the skin of the human body (1,000 to 1,740). That is, in view of thermal effusivity alone, TBAB and water are preferred as the thermal storage material used as a material for the freezing material. Paraffin is less preferred since its low thermal effusivity results in a larger interfacial thermal resistance at the surface in contact with the skin and thus allows heat to be less easily removed.

On the other hand, the melting points (° C.) of the individual thermal storage materials are as follows: TBAB has a melting point of 11.8, water has a melting point of 0, and paraffin has a melting point of 6, 10, or 18. TBAB and paraffin allow for a smaller temperature difference from the surface temperature of the skin. That is, in view of melting point alone, TBAB and paraffin are preferred as the thermal storage material used as a material for the freezing material. Water is less preferred since its low melting point, i.e., 0° C., results in too low a temperature.

As shown above, in view of thermal effusivity and melting point, TBAB is preferred as the thermal storage material used as a material for the freezing material. If a thermal storage material having a thermal effusivity close to that of the skin of the human body is used as the freezing material, the thermal effusivity of the cold storage layer at a border surface in contact with the skin falls within the possible range of thermal effusivity of the skin of the human body. As a result, the condition represented by inequality (5) is satisfied, and the temperature difference from the surface temperature of the skin can be reduced.

According to the literature mentioned above, the skin of the human body has a thermal effusivity of 1,000 to 1,740; therefore, it is more preferred that the cold storage layer have a thermal effusivity of 1,000 to 1,740. However, the cold storage layer only needs to have a thermal effusivity close to that of the skin of the human body, and the condition represented by inequality (5) is satisfied even in the range of 1,000 to 2,000.

The thermal storage material used for the freezing material need not necessarily be TBAB. That is, as indicated by equation (1), the thermal effusivity (b) can be increased by increasing the thermal conductivity (λ). Accordingly, for example, even a material with low thermal effusivity, such as paraffin, can be modified to have properties similar to those of TBAB by adding metal particles so that its thermal effusivity (b) increases, and can thus be used as the freezing material.

(Thermophysical Properties of Cold Storage Layer)

FIG. 7 is an illustration showing a method for calculating the thermal conductivity of a multilayer object. Here, contact resistance is ignored. FIG. 8 is a table showing the thermophysical properties of a cold storage layer. The relationships represented by equations (6) to (8) hold true:

$$\lambda = \alpha \times \rho \times c \quad (6)$$

$$\alpha = \kappa / \rho c \quad (7)$$

$$b = \sqrt{\lambda \times \rho \times c} \quad (8)$$

where λ is the thermal conductivity (W/m·K), α is the thermal diffusivity (m²/s), b is the thermal effusivity (J/(m²·S$^{1/2}$·K)), K is the thermal reflux rate (W/m²·K), ρ is the density (kg·m³), and c is the specific heat capacity (J·kg/K).

Here, "the density and specific heat of the TBAB cold storage layer" are as follows (extracted from "Thermophysical Properties Handbook New Edition", edited by Japan Society of Thermophysical Properties, pp. 161 and 162):

specific heat: c=2,220 J/kg/K, density: ρ=1,082 kg/m³, thickness of cold storage layer: 10 mm The above technique is used to determine the thermophysical properties of the cold storage layer. Here, the thermophysical properties are specified with the TBAB and the cold storage layer packaging material regarded as a single material. Specifically, as shown in FIG. 8, the thermal conductivity (λ) is 0.419, the thermal diffusivity (α) is 1.743×10$^{-7}$, and the thermal effusivity is 1,003.

FIG. 9 is a table showing the thermophysical properties of cold storage layers. The cold storage layers having the configurations shown in FIG. 9 have thermal effusivities in the range of 1,000 to 2,000. The use of such cold storage layers alleviates a thermal imbalance such as the removal of too much heat from the skin of the human body.

(Skin Temperature Measurement Experiment)

FIG. 10A is an illustration (contour plot) showing the results of a skin surface temperature measurement on a human body (arm) wearing the cooling tool according to this embodiment after 10 minutes from the start of the measurement. FIG. 10B is an illustration showing FIG. 10A as a line diagram. In this measurement, a cold storage layer including TBAB in a concentration of 40% by weight packed in 60 μm thick nylon-polyethylene was used. FIGS. 10A and 10B show the states after "0 min" and "10 min" from the start of the measurement. As shown in FIGS. 10A and 10B, the surface temperature of the skin did not fall below 17° C. during cooling with the cooling tool according to this embodiment. This shows that the cooling tool according to this embodiment can be used to perform cooling without causing a stimulus.

Second Embodiment

Figure 11:
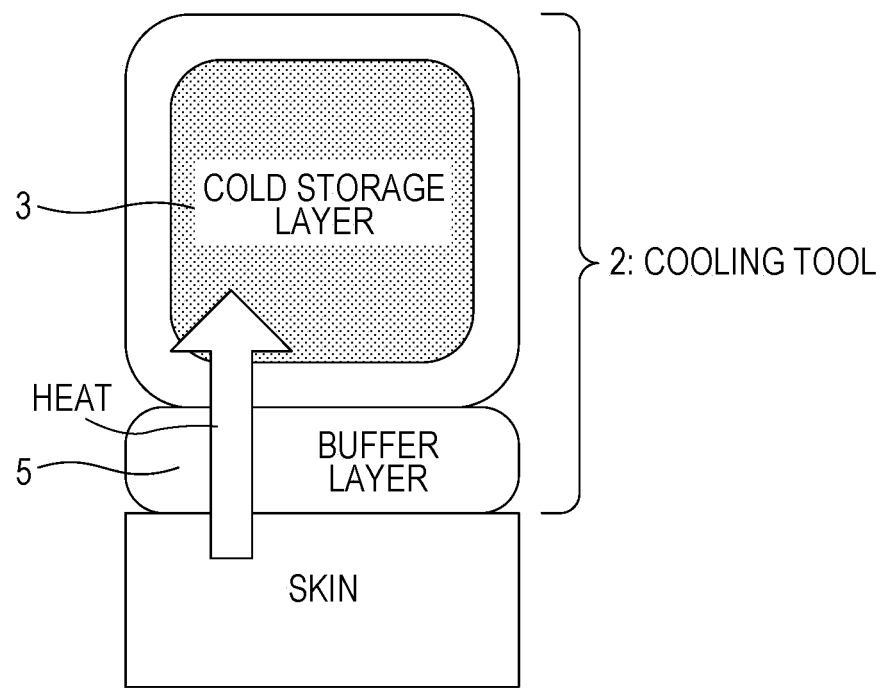
FIG. 11 is an illustration showing the concept of a cooling tool according to a second embodiment.

FIG. 11 is an illustration showing the concept of a cooling tool according to this embodiment. This cooling tool 2 includes a cold storage layer 3 and a buffer layer 5. The thermophysical properties of the cold storage layer 3 are specified as follows: it includes a thermal storage material that has a thermal effusivity within the possible range of thermal effusivity of the skin of the human body. The thermal and mechanical properties of the buffer layer 5 are specified as follows: it is flexible and has a thermal effusivity within the possible range of thermal effusivity of the skin of the human body. The cooling tool 2 according to this embodiment can cool the skin of a human body at a mild temperature for a long period of time without causing discomfort such as feeling too cold when brought into direct contact with the skin of the human body. Furthermore, the buffer layer 5 is flexible and can thus be brought into closer contact with the skin of the human body. This results in a greater cooling effect.

Example 2

Figure 12A:
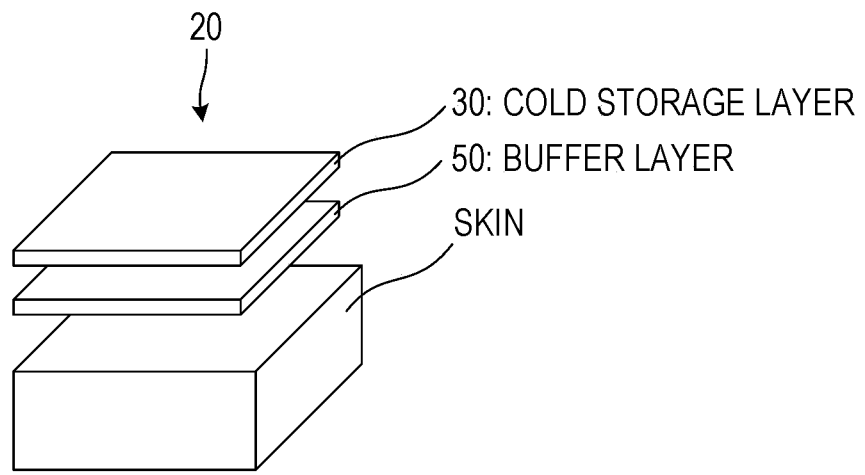
FIG. 12A is a schematic view showing a cooling tool according to Example 2.
Figure 12B:
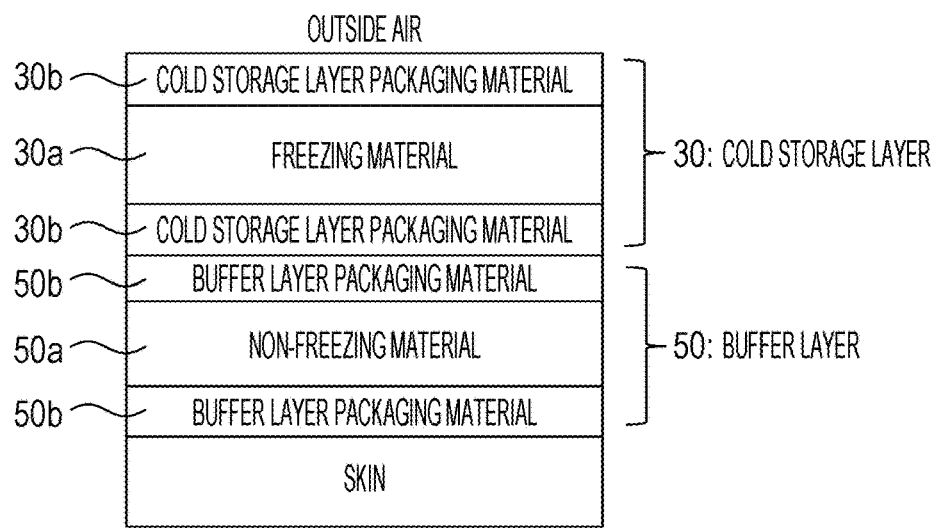
FIG. 12B is a schematic view showing the cooling tool according to Example 2.

FIGS. 12A and 12B are schematic views showing a cooling tool according to Example 2. This cooling tool 20 is composed of a cold storage layer 30 and a buffer layer 50. The configuration of the cold storage layer 30 of the cooling tool 20 according to the second embodiment is similar to that of Example 1; therefore, a description thereof is omitted below. The buffer layer 50 includes a non-freezing material 50a that is flexible at the phase change temperature of the freezing material forming the cold storage layer 30 and a buffer layer packaging material 50b having the non-freezing material 50a packed therein. The buffer layer packaging material 50b forms a second container. The non-freezing material 50a is a thermal storage material that does not freeze at the phase change temperature of the freezing material 30a and that has a thermal effusivity within the possible range of thermal effusivity of the skin of the human body. The non-freezing material 50a used and described in this example is an aqueous solution of sodium chloride (NaCl) in a concentration of 23% by weight; however, the buffer layer need not necessarily include this non-freezing material, but may include any non-freezing material having similar properties. For example, an aqueous solution of potassium chloride (KCl) in a concentration of 23% by weight may be used instead.

Figure 13A:
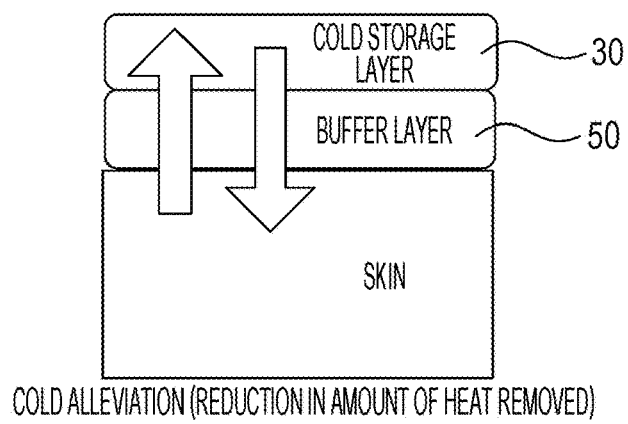
FIG. 13A is an illustration showing the function of a buffer layer.
Figure 13B:
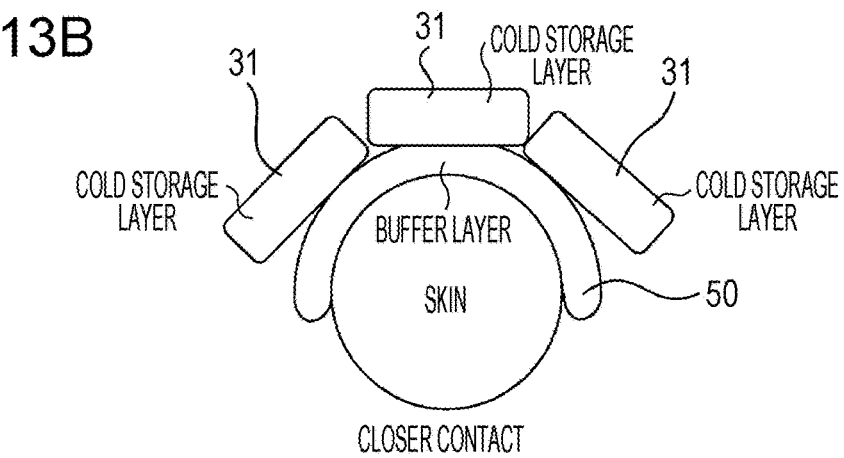
FIG. 13B is an illustration showing the function of the buffer layer.

FIGS. 13A and 13B are illustrations showing the function of the buffer layer 50. As shown in FIG. 13A, the buffer layer 50 is brought into contact with the skin of a human body and transfers heat between the skin of the human body and the cold storage layer 30. In this way, the buffer layer 50 is disposed between the skin of the human body and the cold storage layer 30 and prevents the skin from coming into direct contact with the frozen cold storage layer 30. This prevents rapid removal of heat, thus contributing to cold alleviation (a reduction in the amount of heat removed from the skin). As shown in FIG. 13B, the non-freezing material present in the buffer layer 50 is liquid at the phase change temperature of the freezing material, and the buffer layer packaging material is also flexible, so that the buffer layer 50 can be brought into closer contact with the skin. Alternatively, a plurality of buffer layers may be coupled together by a joint mechanism. In this case, the buffer layers can be coupled in the longitudinal direction or in the lateral direction, or in both directions. Similarly, a plurality of cold storage layers 31 may be coupled together by a joint mechanism. As the temperature of the cold storage layer and the buffer layer increases during the use of the cooling tool, the aqueous solution in each layer accumulates vertically, depending on the orientation of the cooling tool. This results in a difference in heat capacity inside the cooling tool, which leads to "uneven cooling". Even if such a phenomenon occurs in each layer, the difference in heat capacity can be alleviated by coupling a plurality of cold storage layers 31 by a joint mechanism, thus preventing "uneven cooling". Furthermore, the aqueous solution may be thickened so that the shape can be easily maintained in close contact with the skin.

(Thermophysical Properties of Buffer Layer)

As with the cold storage layer, the thermal conductivity of the buffer layer is measured by the method for calculating the thermal conductivity of a multilayer object in FIG. 7. As with the cold storage layer, the relationships represented by equations (6) to (8), where $\lambda$ is the thermal conductivity (W/m·K), a is the thermal diffusivity (m$^2$/s), b is the thermal effusivity (J/(m$^2$·S$^{1/2}$·K)), K is the thermal reflux rate (W/m$^2$·K), $\rho$ is the density (kg·m$^3$), and c is the specific heat capacity (J·kg/K), hold true for the buffer layer.

Here, "the density and specific heat of the buffer layer" are assumed to be equal to those of an aqueous NaCl solution, that is, as follows (extracted from "Thermophysical Properties Handbook New Edition", edited by Japan Society of Thermophysical Properties, pp. 161 and 162):

density: $\rho=1,479$ kg/m$^3$, specific heat: c=3,337 J/kg/K

The above technique is used to determine the thermophysical properties of the buffer layer. Here, the thermophysical properties are specified with the aqueous NaCl solution, the thickener, and the buffer layer packaging material regarded as a single material. FIG. 14 is a table showing the thermophysical properties of the thermal effusivity (b) of buffer layers.

The buffer layers having the configurations shown in FIG. 14 have thermal effusivities in the range of 1,000 to 2,000. These buffer layers have thermal effusivities close to that of the skin of the human body and satisfy the condition represented by inequality (5). That is, the use of such buffer layers alleviates a thermal imbalance such as the removal of too much heat from the skin of the human body.

(Non-Freezing Material)

As shown in the table below, the composition of the non-freezing material may be changed depending on the use situation. Specifically, if the freezing material in the cold storage layer is frozen in a refrigerator (in the temperature range around 4° C.), the non-freezing material used for the buffer layer is "water", "water+thickener", "water+sodium chloride+thickener", or "water+potassium chloride+thickener". In this case, the temperature does not fall below 0° C.; therefore, the non-freezing material in the buffer layer does not freeze even if it is water alone. If the freezing material in the cold storage layer is rapidly frozen in a freezer, the non-freezing material used is "water+sodium chloride+thickener" or "water+potassium chloride+thickener". The freezing material in the cold storage layer can be more quickly frozen in a freezer at −18° C. to 20° C. than in a refrigerator. In this case, the temperature falls below 0° C.; therefore, the buffer layer freezes if it is water alone. To avoid this, sodium chloride or potassium chloride is necessary.

TABLE 2

| Use case | Freezing in refrigerator alone | Freezing in freezer |
|---|---|---|
| Situation | Normal use (freezing in refrigerator) | Rapid freezing (freezing in freezer) |
| Composition of non-freezing material for buffer layer | Water<br>Water + thickener<br>Water + sodium chloride + thickener<br>Water + potassium chloride + thickener | Water + sodium chloride + thickener<br>Water + potassium chloride + thickener |

Example 3

FIGS. 15A and 15B are schematic views showing the configuration of a cooling tool and a treatment tool according to Example 3. The configuration of Example 3 allows the cooling tool according to Example 1 or 2 to be held on part of a human body using a holding member 100. The holding member 100 is composed of, for example, a supporter or a towel. Although the cooling tool shown in FIGS. 15A and 15B is composed only of the cold storage layer 30, it may further include the buffer layer 50 as shown in Example 2. FIG. 15C is an illustration showing an example application. Thus, a treatment tool composed of a cooling tool and a holding member allows for effective cryotherapy.

(Heat-Insulating Material)

Any of the cooling tools of Examples 1 to 3 may include a heat-insulating layer on the side of the cold storage layer facing away from the buffer layer. This avoids heat transfer on the side of the cold storage layer facing away from the skin due to contact with the outside air temperature and thus allows the time for cooling with the cold storage layer to be maintained.

Third Embodiment

FIG. 16 is a schematic view showing the border between a cold storage layer and the skin of a human body. The first embodiment described above assumes that the thermal effusivity of the cold storage material is substantially equal to the thermal effusivity of the skin, that is, "bB=bA" in equation (2), which represents the border temperature $T_{boder}$. Hence, the terms of thermal effusivity are deleted, and the temperature $T_{boder}$ of the border surface is represented by equation (4). In contrast, the third embodiment shows an example in which the temperature $T_{boder}$ of the border surface is calculated without deleting the terms of thermal effusivity.

In equation (2), replacing $T_A$ with $T_{TSM}$ (cold storage material border temperature), $T_B$ with $T_{skin}$ (skin border temperature), $b_A$ with $b_{TSM}$ (cold storage material thermal effusivity), and $b_A$ with $b_{skin}$ (skin thermal effusivity) gives equation (6):

[Math. 6]

$$T_{boder} = T_{TSM} + (T_{skin} - T_{TSM}) \frac{1}{1 + b_{TSM}/b_{skin}} \quad (6)$$

Figure 17:
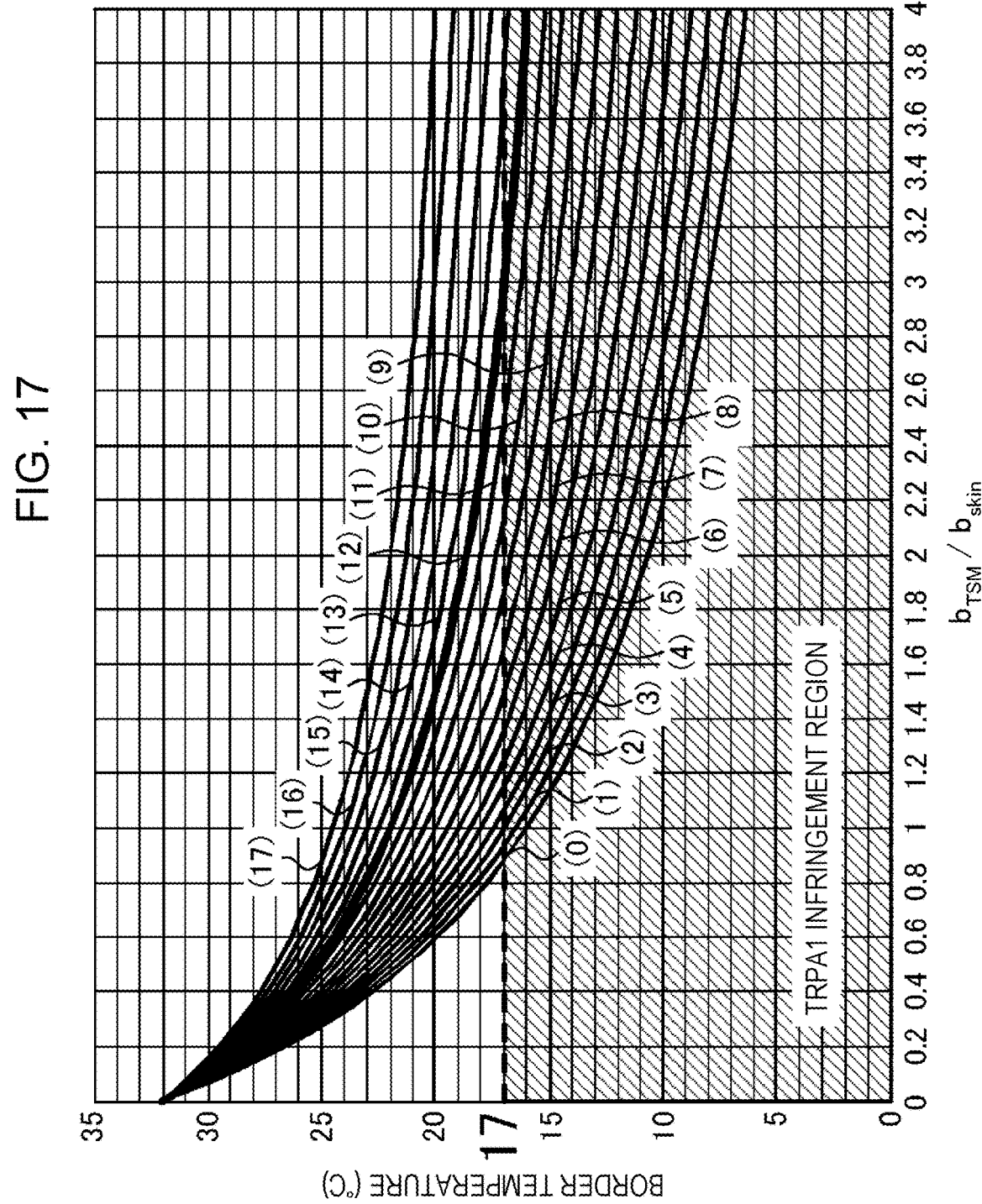
FIG. 17 is a graph showing border temperature and thermal effusivity ratio ($b_{TSM}/b_{skin}$) for different temperatures of cold storage materials.
Figure 19:
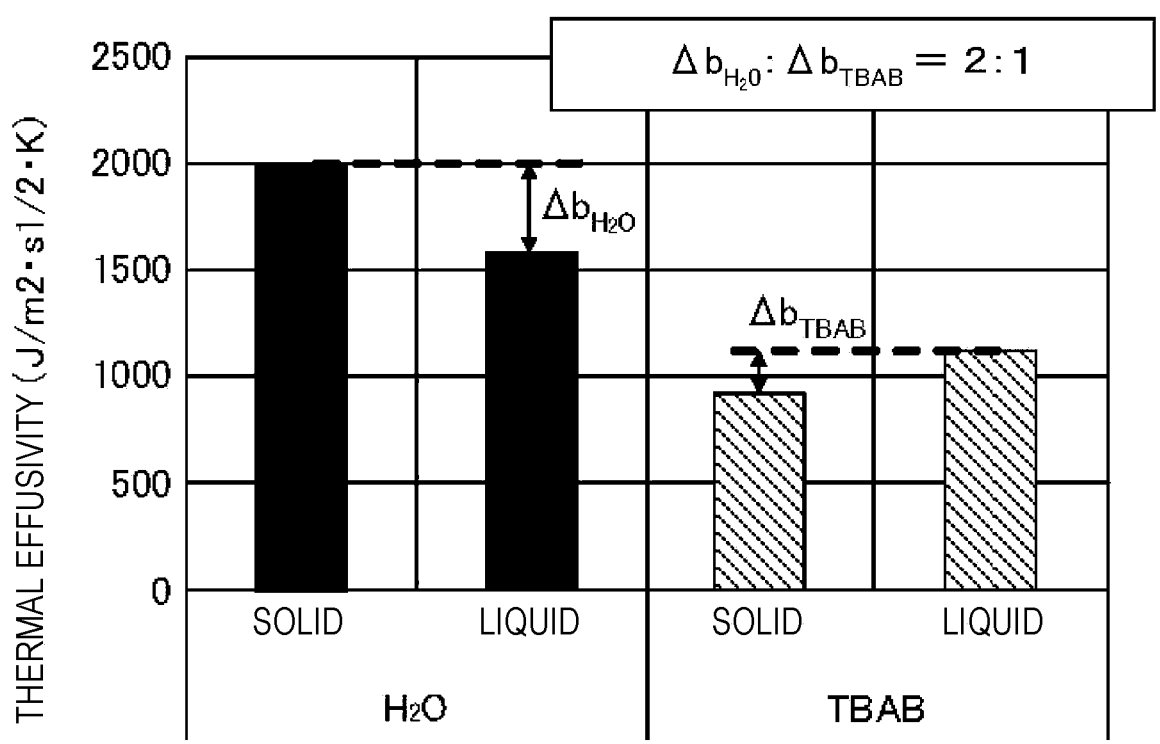
FIG. 19 is a graph showing the results of thermal effusivity measurements for TBAB and water.

FIG. 17 is a graph in which the vertical axis indicates the border temperature and the horizontal axis indicates the thermal effusivity ratio ($b_{TSM}/b_{skin}$) at "$T_{skin}$=32° C. (typical skin surface temperature)" in equation (6) for different "$T_{TSM}$ (cold storage material border temperatures)" of cold storage materials from (0) to (17). The ranges on the vertical and horizontal axes in FIG. 17 are given by way of example with reference to a temperature range where "0° C. corresponds to ice and 12° C. corresponds to the thermal storage material according to this embodiment". If conditions under which the border temperature does not fall within the range of "17° C. or lower" in FIG. 17 are satisfied, a cold storage material that does not express TRPA1 can be achieved. The contents of FIG. 19 are given by way of example only; values outside this range are also possible as long as TRPV1 is not infringed.

Fourth Embodiment

Figure 18:
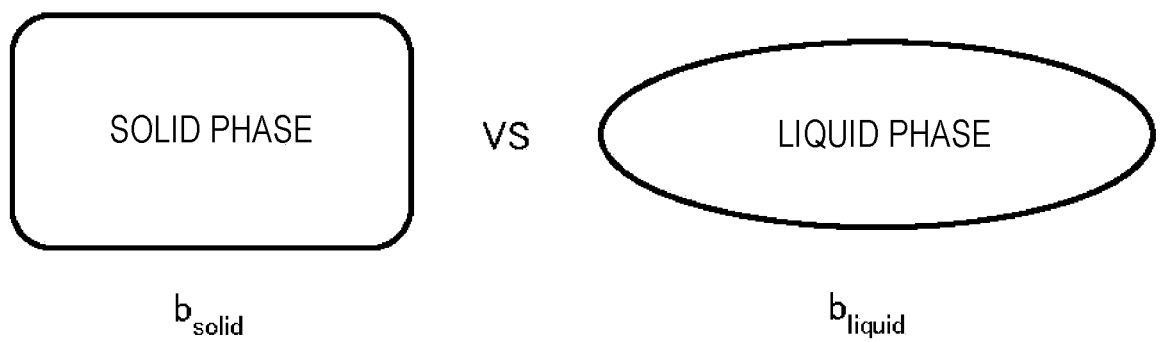
FIG. 18 is an illustration showing the concept of a solid phase ($b_{solid}$) and a liquid phase ($b_{liquid}$).

In the fourth embodiment, as shown in FIG. 18, "water" and "clathrate hydrate (in this embodiment, TBAB)" are used for comparison between the thermal effusivity of cold storage materials in "solid phase ($b_{solid}$)" and the thermal effusivity of cold storage materials in "liquid phase ($b_{liquid}$)" to demonstrate that clathrate hydrates are advantageous over water from measurement results. The thermal effusivity is measured by comparing the thermal effusivity of a 40% by weight aqueous solution of TBAB as measured by the hot disk method with a literature value for water (from "Heat Transfer Engineering" published from The Japan Society of Mechanical Engineers).

The conditions for the thermal effusivity measurement on TBAB are as follows. Specifically, the sample was "40% by weight aqueous solution of tetrabutylammonium bromide". The measurement instrument was "Hot disk (manufactured by Kyoto Electronics Manufacturing Co., Ltd.)". The measurement results are shown in FIG. 19. The difference between the solid and liquid phases of water, "$\Delta b_{H2O}$", and the difference between the solid and liquid phases of TBAB, "$\Delta b_{TBAB}$", were expressed as "$\Delta b_{H2O}:\Delta b_{TBAB}$=2:1". These measurement results show that there is a smaller difference in thermal effusivity between the solid and liquid phases of a clathrate hydrate (TBAB) than between the solid and liquid phases of water. Thus, there is a smaller difference in the way heat is removed between the solid and liquid phases of a clathrate hydrate than between the solid and liquid phases of water, so that a clathrate hydrate can cool a human body without a noticeable difference in the way they feel during cooling.

One aspect of the present invention can employ the following configuration. Specifically, (A) a cooling tool according to one aspect of the present invention is a cooling tool for cooling a human body, including a freezing material that undergoes a phase change at a particular temperature and a first container containing the freezing material. The first container transfers heat between the human body and the freezing material at a contact surface in contact with the skin of the human body. At least the contact surface has a thermal effusivity within the possible range of thermal effusivity of the skin of the human body.

Thus, at least the contact surface of the first container in contact with the skin of the human body has a thermal effusivity within the possible range of thermal effusivity of the skin of the human body, which results in a reduced thermal resistance at the interface between the skin of the human body and the cooling tool. As a result, the human body is unlikely to feel pain during use.

(B) A cooling tool according to one aspect of the present invention is a cooling tool for cooling a human body, including a freezing material that undergoes a phase change at a particular temperature and a first container containing the freezing material. The first container transfers heat between the human body and the freezing material at a contact surface in contact with the skin of the human body. The contact surface has a thermal effusivity ($J/(m^2 \cdot S^{1/2} \cdot K)$) of 1,000 to 2,000.

This configuration results in a reduced thermal resistance at the interface between the skin of the human body and the cooling tool, so that the human body is unlikely to feel pain during use.

(C) A cooling tool according to one aspect of the present invention satisfies the following equation:

$$T_{boder} = \frac{T_{skin} + T}{2} \quad \text{[Math. 7]}$$

where $T_{TSM}$ is the temperature of the freezing material, $T_{skin}$ is the surface temperature of the skin of the human body, and $T_{boder}$ is the temperature of the contact surface.

Thus, if the thermal effusivity of the cold storage layer is specified as substantially equal to the thermal effusivity of the skin of the human body, it is possible to alleviate a thermal imbalance such as the removal of too much heat by the cold storage layer.

(D) In a cooling tool according to one aspect of the present invention, the temperature $T_{TSM}$ of the freezing material is 12° C.±2° C.

The use of such a freezing material having a melting point of 12° C. alleviates the temperature difference between the skin of the human body and the cold storage layer, thus eliminating discomfort due to cold stimuli.

(E) A cooling tool according to one aspect of the present invention is a cooling tool for cooling a human body, including a freezing material that undergoes a phase change at a particular temperature; a first container containing the freezing material and forming a cold storage layer; a non-freezing material that is flexible at the phase change temperature of the freezing material; and a second container containing the non-freezing material and formed of a flexible material. The second container transfers heat between the human body and the non-freezing material at a contact surface in contact with the skin of the human body. At least the contact surface has a thermal effusivity within the possible range of thermal effusivity of the skin of the human body.

Thus, at least the contact surface of the second container in contact with the skin of the human body has a thermal effusivity within the possible range of thermal effusivity of the skin of the human body, which results in a reduced thermal resistance at the interface between the skin of the human body and the cooling tool. As a result, the human body is unlikely to feel pain during use. Furthermore, the non-freezing material and the second container are flexible and can thus be brought into closer contact with the skin of the human body. This results in a greater cooling effect.

(F) A cooling tool according to one aspect of the present invention is a cooling tool for cooling a human body, including a freezing material that undergoes a phase change at a particular temperature; a first container containing the freezing material and forming a cold storage layer; a non-freezing material that is flexible at the phase change temperature of the freezing material; and a second container containing the non-freezing material, formed of a flexible material, and forming a buffer layer. The second container transfers heat between the human body and the non-freezing material at a contact surface in contact with the skin of the human body. The contact surface has a thermal effusivity $(J/(m^2 \cdot S^{1/2} \cdot K))$ of 1,000 to 2,000.

This configuration results in a reduced thermal resistance at the interface between the skin of the human body and the cooling tool, so that the human body is unlikely to feel pain during use.

(G) A cooling tool according to one aspect of the present invention satisfies the following equation:

$$T_{boder} = \frac{T_{skin} + T}{2}$$ [Math. 8]

where T is the temperature of the buffer layer, $T_{skin}$ is the surface temperature of the skin of the human body, and $T_{boder}$ is the temperature of the contact surface.

Thus, if the thermal effusivity of the buffer layer is specified as substantially equal to the thermal effusivity of the skin of the human body, it is possible to alleviate a thermal imbalance such as the removal of too much heat by the cold storage layer.

(H) A treatment tool according to one aspect of the present invention is a treatment tool used in cryotherapy, including the cooling tool according to any one of (A) to (G) above and a holding member that holds the cooling tool in contact with the skin of a human body.

This configuration results in a reduced thermal resistance at the interface between the skin of the human body and the cooling tool, so that the human body is unlikely to feel pain during use.

As described above, the cooling tool according to this embodiment can cool a human body at an appropriate temperature and can cool the skin of the human body at a mild temperature for a long period of time without causing discomfort such as feeling too cold when brought into direct contact with the skin of the human body.

This international application claims priority to Japanese Patent Application No. 2016-227104, filed on Nov. 22, 2016, the entire contents of which are incorporated herein by reference.

REFERENCE SIGNS LIST 1 cooling tool
2 cooling tool
3 cold storage layer
5 buffer layer
10 cooling tool
30 cold storage layer
30a freezing material
30b cold storage layer packaging material
31 cold storage layer
50 buffer layer
50a non-freezing material
50b buffer layer packaging material

The invention claimed is:
1. A cooling tool for cooling a human body, comprising:
a freezing material that undergoes a phase change at a particular temperature; and
a first container containing the freezing material,
wherein the first container transfers heat between the human body and the freezing material at a contact surface in contact with a skin of the human body,
at least the contact surface has a thermal effusivity within a range of thermal effusivity of the skin of the human body, and
the cooling tool satisfies the following equation:

$$T_{boder} = \frac{T_{skin} + T_{TSM}}{2},$$

where $T_{TSM}$ is a temperature of the freezing material, $T_{skin}$ is a surface temperature of the skin of the human body, and $T_{boder}$ is a temperature of the contact surface.

2. The cooling tool according to claim 1, wherein the contact surface has a thermal effusivity $(J/(m^2 \cdot S^{1/2} \cdot K))$ of 1,000 to 2,000.

3. The cooling tool according to claim 1, wherein the temperature $T_{TSM}$ of the freezing material is 12° C.±2° C.

4. A cooling tool for cooling a human body, comprising:
a freezing material that undergoes a phase change at a particular temperature;
a first container containing the freezing material and forming a cold storage layer;
a non-freezing material that is flexible at the phase change temperature of the freezing material; and
a second container containing the non-freezing material, comprising a flexible material, and forming a buffer layer,
wherein the second container transfers heat between the human body and the non-freezing material at a contact surface in contact with a skin of the human body,
at least the contact surface has a thermal effusivity within a range of thermal effusivity of the skin of the human body, and
the cooling tool satisfies the following equation:

$$T_{boder} = \frac{T_{skin} + T}{2},$$

where T is a temperature of the buffer layer, $T_{skin}$ is a surface temperature of the skin of the human body, and $T_{boder}$ is a temperature of the contact surface.

5. The cooling tool according to claim 4, wherein the contact surface has a thermal effusivity ($J/(m^2 \cdot S^{1/2} \cdot K)$) of 1,000 to 2,000.

6. A treatment tool used in cryotherapy, comprising:
the cooling tool according to claim 1; and
a holding member that holds the cooling tool in contact with the skin of the human body.

* * * * *